United States Patent [19]
Martin et al.

[11] Patent Number: 5,518,989
[45] Date of Patent: May 21, 1996

[54] SEED VIGOR BY PRE-HARVEST DEFOLIATION OF MAIZE PLANTS

[75] Inventors: Barry Martin, Urbandale; John Schoper, Johnston, both of Iowa; Laurie Carrigan, Spicer, Minn.

[73] Assignee: Pioneer Hi-Bred International, Des Moines, Iowa

[21] Appl. No.: 189,231

[22] Filed: Jan. 31, 1994

[51] Int. Cl.⁶ .......................... A01N 43/40; A01N 57/12
[52] U.S. Cl. .................... 504/116; 504/162; 504/165; 504/167; 504/168; 504/206; 504/235; 504/250; 47/58
[58] Field of Search .......................... 504/116, 162, 504/165, 167, 168, 206, 235, 250; 47/58

[56] References Cited

PUBLICATIONS

Adegbuyi et al. "Effects of Seed Vigor on Crop Characters in Uniform and Reduced Populations of Corn (Zea Mays L.)", *J. Agronomy & Crop Science*, 162: 10–20 (1989).
Adegbuyi et al. "Field Criterial Used in Determining the Vigor of Seed Corn (Zea mays L.) . . . ", *J. Agronomy & Crop Science*, 161: 171–177 (1988).
Coggin et al. "Effects of Depodding and Defoliation on the Yield and Quality of Lima Beans", *J. Econ. Entomol.*, 73;(4):609–614 (Aug. 1980).
Crookston et al. "Early Defoliation Affects Corn Grain Yields", *Crop Science*, 18:485–489 (May–Jun. 1978).
Hicks et al. "Defoliation Effects on Corn Hybrids Adapted to the Northern Corn Belt", *Agronomy Journal*, 69:387–390 (May–Jun. 1977).
Hunter et al. "Corn Seed Maturity Indicators and Their Relationship to Uptake . . . ", *Crop Science*, 31:1309–1313 (1991).
Johnson et al. "Growth and Yield of Maize as Affected by Early–Season Defoliation", *Agronomy Journal*, 70:995–998 (Nov.–Dec. 1978).
Martin et al. "Relationships between Laboratory Germination Tests and Field Emergences of . . . ", *Crop Science*, 28(5):801–805 (Sep.–Oct. 1988).
Mesa et al. "Plot Type and Treatment for Assessment of Soybean Response to Defoliation", *Crop Science*, 24:847–850 (Sep.–Oct. 1984).
Onofre et al. "Defoliacion a Partir De Antesis, Rendimiento De Grano Y Distribucion Final De Materia . . . ", *Agrociencia*, 65: 253–262 (1987).
Prokof'ev et al. "Influence of 'Mild' Defoliation on the Yield and Quality of Sunflower Seeds", Translated from *Prikladnaya Biokhimiya i Mikrobiologiya*, 8(4):402–406 (Jul.–Aug. 1972).
Saleh et al. "Response of Rice, Maize, Sorghum, Groundnut and Soybean to Foliage Losses", *1974 Yearbook, Indonesia Centr. Inst. for Agri.*, pp. 185–189, (1974).
Tekrony et al. "Relationship Between Laboratory Indices of Soybean Seed Vigor and Field Emergence", *Crop Science*, 17:573–577 (Jul.–Aug. 1977).
Tollenaar et al. "Effects of Defoliation on Kernel Development in Maize", *Canadian Journal of Plant Science*, 58: 207–212 (1978).
Vieira et al. "Effect of Drought and Defoliation Stress in the Field on Soybean Seed Germination . . . ", *Crop Science*, 32:471–475 (Mar.–Apr. 1992).

*Primary Examiner*—S. Mark Clardy
*Assistant Examiner*—Brian G. Bembenick
*Attorney, Agent, or Firm*—Foley & Lardner

[57] ABSTRACT

An increase in the quality of maize seed, especially with respect to improved seed vigor, is achieved by defoliating maize plants during a specific period after pollination. A maize seed assemblage then is obtained that is characterized by an enhanced seed vigor.

7 Claims, No Drawings

SEED VIGOR BY PRE-HARVEST DEFOLIATION OF MAIZE PLANTS

BACKGROUND OF THE INVENTION

1. Field of the Invention

This invention is directed to a novel method for enhancing the quality of maize seed. In particular, this invention is directed to a method of improving maize seed vigor by defoliating maize plants after pollination. This invention also is directed to a maize seed assemblage characterized by an increased seed vigor, which can be obtained using the disclosed method.

2. Background

The quality of seed is of major concern in agriculture throughout the world. Seed quality is subject to legislative control and certification schemes in most developed countries. Forbes et al., PLANTS IN AGRICULTURE, Cambridge University Press (1992). In systems of "subsistence" agriculture, especially in the developing world, poor seed quality is a major limitation to productivity. Id.

One important factor in determining the quality of maize seed is the maturity of the seed at the time of harvest. Often, maize seed is harvested before the seed reaches optimal maturity. Reasons for premature harvest include frost risk, production plant capacity, and the need for time to move seed from a site of production in the southern hemisphere to a planting site in the northern hemisphere. In addition, many varieties of inbred lines of maize do not mature in a uniform fashion throughout the field, resulting in a seed harvest containing poor quality seed.

Seed quality is typically measured by standard germination tests. Delouche et al., *Proc. Assoc. Off. Seed Anal.* 50:124 (1960); Woodstock, *Seed World* 97:6 (1965). While the results of a standard germination test may correlate well with field emergence when soil conditions are favorable for rapid emergence, the test cannot predict field performance when soil and environmental conditions impose stress on the germinating seeds, as often occurs with early planting. Tekrony et al., *Crop Sci.* 17:573 (1977).

The concept of "seed vigor" evolved to compensate for the failure of standard germination tests to predict field performance under conditions of environmental stress. Adegbuyi et al., *J. Agron. & Crop Sci.* 161:171 (1988). Seed vigor is a reflection of those properties that determine the potential for rapid, uniform emergence of plants and the development of normal seedlings under a wide range of field conditions. 1983 SEED VIGOR TESTING HANDBOOK (Assoc. Official Seed Analysts). Seed vigor is thought to influence not only emergence and emergence rate but also plant height, stem diameter, shoot dry matter, leaf length and leaf width. Adegbuyi et al. *J. Agronomy & Crop Science* 161:171 (1988).

The quality of seed vigor is particularly important where a crop is grown near the limits of its climatic tolerance range or sown into adverse soil conditions. In the northern U.S. corn belt and in Europe, maize is generally planted in the early spring into soils that are, or may become, too cold and wet for optimal germination. Thus, there is a need for a method to increase the quality of maize seed, as measured by seed vigor.

There has been extensive study of the effects of crop defoliation on yield and seed quality. See, e.g., corn: Hicks et al., *Agronomy J.* 69:387 (1977), Tollenaar et al., *Can. J. Plant Sci.* 58:207 (1978), Crookston et al., *Crop Sci.* 18:485 (1978), Johnson, *Agronomy J.* 70:995 (1978), Hunter et al., *Crop Sci.* 31:1309 (1991); sunflower: Prokof'ev et al., *Prik. Biokhimiya Mikrobiol.* 8:402 (1972); soybean: Mesa et al., *Crop Sci.* 24:847 (1984), Vieira et al., *Crop Sci.* 32:471 (1992); sorghum: Onofre et al., *Agrociencia* 65:253 (1987); lima bean: Coggin et al., *J. Econ. Entomol.* 73:609 (1980). See also Saleh et al. in 1974 YEARBOOK, Indonesian Central Institute for Agriculture (rice, maize, sorghum, groundnut and soybean). The overall tenor of this body of literature is that defoliation, while unavoidable and deleterious in certain contexts, actually may have an advantageous effect, for example, with regard to increased oil content/yield of sunflower seeds. Prokof'ev et al., supra.

Moreover, Crookston et al., supra, report that defoliation can enhance yield in short-season maize hybrids. Crookston et al. found that, although leaf removal during silking consistently led to a reduction in maximum yield, defoliation at a very early growth stage, prior to flowering, enhanced yield. It has not been possible, however, to predict whether defoliation prior to flowering could provide enhanced seed vigor, since yield and seed vigor are not clearly correlated in maize. Adegbuyi et al., *J. Agronomy and Crop Science* 162:10 (1989).

SUMMARY OF THE INVENTION

Accordingly, it is an object of the present invention to improve the overall vigor of harvested seed in a crop by defoliating the crop during a critical period.

It is a further object of this invention to produce a more uniform maturation of seed in a population of maize plants to enhance seed vigor of the harvested seed.

These and other objects are achieved, in accordance with one embodiment of the present invention, by the provision of a method for treating a stand of maize plants, comprising the steps of (A) reducing functional leaf area in substantially all of the plants, wherein the reduction in functional leaf area is effected at between about 600 and about 850 GDDs after pollination of the plants, and then (B) harvesting the stand, such that a seed assemblage is obtained from the stand that is characterized by a level of seed vigor that is enhanced relative to the level of seed vigor in a seed assemblage harvested from a comparison stand of maize plants not subjected to the reducing of functional leaf area.

In accordance with another embodiment of the present invention, a maize seed assemblage is provided that is characterized by increased seed vigor.

DETAILED DESCRIPTION OF PREFERRED EMBODIMENTS

There is little description in the literature regarding the effect of defoliation upon seed vigor. In a rare study on seed vigor, Vieira et al., supra, found that defoliation of soybean resulted in underdeveloped seeds characterized by reduced seed germination and vigor.

In marked contrast to the negative findings of Vieira et al., the present inventors made the surprising finding that defoliation can be used as a tool to obtain an enhanced vigor of maize seed by properly balancing hastened maturity of the seed and smaller seed size. However, the inventors discovered that defoliation must be performed during a critical period in the maturation of the maize crop, as described herein.

According to the invention, a stand of maize plants is treated to reduce the functional leaf area in substantially all of the plants. A "stand" refers to a living assemblage of maize plants. A stand can be quantitated by determining the total dry mass of maize plants in an area. The "functional leaf area" of a plant refers in the present description to the total area of leaf that is capable of intercepting sunlight. The functional leaf area is reduced by eliminating all leaves of the plants, or by eliminating all leaves above the ear including the ear leaf.

"Substantially all of the plants" refers in the present description to at least 99% of the maize plants in the stand.

In the present context, "seed assemblage" denotes a collection of seed harvested from a stand of maize plants.

The methodology of the present invention can be used to produce a seed harvest that is characterized by an increased seed vigor, as determined by a seed vigor test. "Seed vigor" refers to a collection of properties that determine the potential for rapid, uniform emergence of plants and the development of normal seedlings under a wide range of field conditions. The degree of seed vigor possessed by a given seed assemblage can be determined by a variety of techniques. 1983 SEED VIGOR TESTING HANDBOOK, supra. For example, seed vigor can be determined by observing early stand count or by observing the amount of vegetative growth produced by the seeds after emergence at the seedling stage, as described in Example 2, herein.

Alternatively, seed vigor can be evaluated using an in vitro germination test. For example, the Pioneer Cold Test can be used to predict how maize seed will perform in a cold, wet environment. See Martin et al., *Crop Sci.* 28:801–805 (1988), and Example 1 below.

The soak test is an alternative in vitro germination test which can be used to identify less cold-tolerant inbred lines. Martin et al., supra. Briefly, the soak test is performed by soaking seeds in deionized water and then, rolling the seeds between two pieces of heavyweight germination paper. The rolled seeds are incubated for five days at 27° C. and germinated seeds are counted.

The present inventors discovered that defoliation of maize plants can enhance seed vigor if the defoliation is performed during a particular period after pollination. Defoliation after the critical period will not produce an enhancement of seed vigor, while defoliation before the critical period will result in an unacceptable reduction in seed size. This critical period is determined by measuring "growing degree days" (GDDs). The GDD system is a standard among systems for maturity rating in corn. See, for example, Eckert et al. in the 1986 NATIONAL CORN HANDBOOK, page 1017. The significance of the GDD is that it takes a certain number of GDDs for a given inbred or hybrid to reach a particular stage of plant development.

As used herein, GDDs are calculated by the Barger Method in which the heat units for a 24-hour period are calculated by using the formula:

$$GDD = \frac{(\text{Maximum °F.} + \text{Minimum °F.})}{2} - 50.$$

Barger, *Weekly Weather Crop Bulletin* 56:10 (May 5, 1969).

According to the present invention, defoliation must be performed from about 600 GDDs post-pollination to about 850 GDDs post-pollination. In general, the extent of seed vigor enhancement is inversely related to the number of GDDs post-pollination at the time of defoliation. Therefore, one can obtain the greatest enhancement in seed vigor by defoliating at 600 GDDs post-pollination, which is the earliest time in the 600 to 850 GDD window. However, the cost of increased seed vigor induced by such early defoliation is a potential decrease in seed size. The size of seeds in a maize seed harvest is an important commercial consideration because larger seed size is preferred in the marketplace. Therefore, the precise time of defoliation chosen will reflect a balance between the desired enhancement in seed vigor and the desired seed size.

Since genotype determines the rate of the maturation of maize seed and the rate of seed size increase, the time of defoliation must be determined for each particular maize hybrid. Generally, hybrids that flower earlier tend to have seeds that increase in size and mature rapidly. Table 1 provides a general guideline for choosing the time of defoliation. Typically, the defoliated plants provide a maize seed harvest characterized by increased seed vigor and a loss in seed size of about 10 percent, as measured by kernel dry weight.

TABLE 1

| GUIDELINES FOR CHOOSING TIME OF DEFOLIATION | |
|---|---|
| GDD to Flowering | Time of Defoliation (GDD Post-Pollination) |
| 1100 | 600 |
| 1200 | 650 |
| 1300 | 700 |
| 1400 | 750 |
| 1500 and later | 800 |

According to the present invention, defoliation can be performed by a variety of methods. For example, defoliation can be performed by a mechanical means. One such method of defoliation is manual defoliation, as illustrated in Examples 1 and 2, below.

Alternatively, defoliation can be performed using the application of chemicals, such as a herbicidal formulation. Any herbicide can be used for a herbicidal formulation in the practice of the present invention. Preferred herbicides include herbicides that (1) are characterized by a low residual toxicity, (2) are not translocated to the ear and (3) are effective as defoliants in a variety of environmental conditions.

Examples of herbicides that are appropriate for a herbicidal formulation include Paraquat, 1,1'-dimethyl-4,4'-dipyridinium (ICN Biochemicals, Inc.); Roundup®, mono(isopropylamine) salt of N-(phosphonomethyl)glycine (Monsanto Chemical Company); Ignite®, monoamonium 2-amino-4-[(hydroxy)methyl- phosphinyl]-butanoate (Hoechst-Roussel Agri-Vet Company); and Diquat, 1,1'-ethylene-2,2'-dipyridinium (Valent U.S.A. Corporation). Preferred herbicides include Paraquat, Ignite® and Diquat.

In the practice of the present invention, plants are treated with herbicides according to the manufacturers' instructions. Typical modes of herbicide application are illustrated in Examples 2 and 3, below.

A herbicidal formulation also can include a surfactant to improve the uptake of the herbicide by the maize plant. Examples of anionic surfactants include calcium and amine salts of dodecylbenzene sulfonic acid and sodium diisoethylsulfosuccinate. Examples of cationic surfactants include aliphatic mono-, di-, or polyamine as an acetate or oleate.

Nonionic surfactants are preferred. Examples of nonionic surfactants include the condensation products of fatty acid esters, fatty alcohols, fatty acid amides or fatty amines with ethylene and/or propylene oxide, alkyl, alkenyl, or polyaryl-substituted phenols with ethylene an/or propylene oxide, and fatty esters of polyhydric alcohol ethers, such as sorbitan fatty acid esters, condensation products of such esters with ethylene oxide including polyoxyethylene sorbitan fatty acid esters, block copolymers of ethylene oxide and propylene oxide, ethoxylated lanolin alcohols or ethoxylated lanolin acids.

Representative nonionic surfactants include PG 26-2®, a secondary butyl (((phenoxy(polypropylene)oxy) polyethylene)oxy)ethanol (The Dow Chemical Company); Silwet L-77®, a nonionic silicone glycol copolymer (Union Carbide Corporation); and Triton (Ortho) X-77®, alkylarylpolyoxyethylene glycol (Chevron Chemical Company). X-77® is a particularly preferred surfactant. The choice of a suitable surfactant is well within the capabilities of one skilled in the art.

The amount of surfactant present in a concentrated herbicidal composition will generally be in the range of from about 0 percent to about 5 percent, preferably from about 0 percent to about 0.5 percent by weight of the final herbicidal formulation.

The present invention, thus generally described, will be understood more readily by reference to the following examples, which are provided by way of illustration and are not intended to be limiting of the present invention.

EXAMPLE 1

Effect of Manual Defoliation at 600 GDD Post-Pollination Upon Seed Vigor

In these studies, fifteen inbreds were grown in isolated fields in Willmar, Minn. The inbreds included: R19, W03, W63, K76, W80, G50, J40, P02, M63, K74, W86, M10, G47 and W06. In the experimental groups, defoliation was performed at 600 GDD post-pollination by manually stripping all leaves from the plants. Control groups were not defoliated.

The effect of defoliation upon seed maturation was evaluated using either the milk line method or by observation of the appearance of seed black layer. The milk line method for determining seed maturity is based upon the progressive solidification of the milky endosperm which begins at seed's apex and ends at the seed base. For example, the milk line is present at approximately one-fourth of the way down from the apex at the 75% milk line stage, while the milk line is present at the midpoint of the seed at the 50% milk line stage. The disappearance of seed milk is coincident with the cessation of seed dry weight increase and physiological maturity. The black layer method of assessing seed maturity is based upon the development of a black layer in the placental-chalazal region of the seed. The appearance of the black layer indicates the completion of seed maturation.

To evaluate the effects of defoliation on seed vigor, seed was harvested at 100 GDD intervals from 600 GDD post-pollination to 1000 GDD post-pollination. Seed quality was examined using the Pioneer Cold Test. Martin et al., *Crop Sci.* 28:801–805 (1988). Briefly, the Cold Test was performed by evenly distributing a thin layer of sandy-loam soil on wet germination paper and then, chilling the soil and germination paper at 10° C. for 24 hours. The soil and germination paper were kept wet by cloth wicks which extended from the paper to a reservoir of water. Four replications of the test seeds were placed embryo-side down onto the soil, and the seeds were incubated at 10° C. for seven days. Then, the seeds were transferred to 27° C., 85% relative humidity for three days. Seed vigor was determined by calculating the percentage of germinated seeds.

The results of these experiments demonstrated that defoliation at 600 GDD increased the rate of seed maturation. The non-defoliated control inbreds reached the 75% milk line stage at 760 GDD post-pollination, while defoliated inbreds reached the 75% milk line stage at 700 GDD post-pollination. Control inbreds reached the 50% milk line stage at 840 GDD post-pollination, while defoliated inbreds reached the same stage at 770 GDD post-pollination. Similarly, the non-defoliated control inbreds reached the black layer stage at 960 GDD post-pollination, while defoliated inbreds reached the black layer stage at 890 GDD post-pollination. Thus, defoliation increased the rate of seed maturity by about 70 GDD, which was the equivalent of six to eight days under the conditions of this study.

In addition, the results of the Cold Test showed an enhanced vigor of seeds harvested from defoliated plants, compared with seeds harvested from non-defoliated control plants. See Table 2. Thus, defoliation at 600 GDD post-pollination provided an enhanced seed vigor as well as an increase in the rate of seed maturity.

TABLE 2

VIGOR OF SEED AT 700–1000 GDDs POST-POLLINATION AS MEASURED BY THE PIONEER COLD TEST

| Inbred:Treatment | | Cold Test Results (% Germination) | | | |
|---|---|---|---|---|---|
| | | 700 GDD | 800 GDD | 900 GDD | 1000 GDD |
| R19: | Control | 59 | 65 | 92 | 87 |
| | Defoliation | 63 | 82 | 94 | 95 |
| W63: | Control | 60 | 77 | 79 | 73 |
| | Defoliation | 51 | 76 | 91 | 90 |
| K76: | Control | 20 | 41 | 86 | 82 |
| | Defoliation | 25 | 74 | 93 | 88 |
| W80: | Control | 38 | 87 | 92 | 83 |
| | Defoliation | 59 | 93 | 95 | 95 |

EXAMPLE 2

Effect of Manual and Chemical Defoliation at 750 or 850 GDD Post-Pollination Upon Seed Vigor In these studies, twenty inbreds were used as females in two isolated fields in Kekaha, Hi. One field contained a W52 male and the following females: M49, G29, W30, R03, MJ8, V78, BW6, N46, W78 and AB6. The other field contained a P03 male and the following females: W52, K29, W61, T10, P85, R41, J01, K35, AB5 and HR1 females. Both isolated fields were planted on November 19 and all inbreds were silking by January 17. Post-pollination GDDs were counted beginning on January 20.

Control groups were not defoliated. In experimental groups, plants were defoliated at about 750 and about 850 GDD post-pollination. Defoliation was performed by stripping leaves by hand or by chemical treatment. Manual defoliation was performed by breaking the flag leaf from the midrib to the ear node. Chemical defoliation treatments included: 24 ounces of Paraquat (ICN Biochemicals, Inc.)/acre, or 15 ounces of Roundup® (Monsanto Chemical Co.) plus one pint X-77® (Chevron Chemical Company)/acre. Chemicals were applied using a John Deere 6000 Hi cycle sprayer, with two spray drops 28 inches long, one nozzle over row, 30 psi 11004 flat fans at a spray speed of 3.5 mph. Twenty gallons of water were used for each 0.264 acre.

To test the effects of defoliation on seed vigor, seed was harvested either at seed maturity or before seed maturity. Groups of maize seed were harvested at maturity as determined by the observation of black layer formation. In these studies, the black layer stage occurred at 1120–1200 GDD post-pollination. At this stage of maturity, 20–28% of the endosperm was solid, as determined by a GAC II moisture meter (Dickey-John).

In the group of early-harvested maize, ears were harvested at the 50% milk line stage. In these studies, the 50% milk line stage occurred at 906–1050 GDD post-pollination. At this stage of maturity, 35–40% of the endosperm was solid, as determined by a GAC II moisture meter (Dickey-John).

Seed quality was tested using a field emergence test. In these studies, seeds were planted on April 5 in a nursery in Johnston, Iowa as three replicates of 50 kernels. The average daily high temperature was 15.5° C. and the daily low was 5° C. prior to emergence. First emergence was recorded on April 30, which was 190 GDD after planting.

Early stand count and seedling vigor were recorded at the V3 stage in which the seedling presented three, fully expanded leaves. Early stand count was calculated as the number of surviving plants. Seedling vigor was determined by using a visual rating of one to nine of the amount of vegetative growth after emergence at the seedling stage in which the plant typically contains about five leaves. A higher score indicates better vigor. The seedling vigor rating is based upon a judgment of the uniformity of emergence, plant height, and mass of green leaf tissue.

Seed dry weight was calculated by drying the seeds for 72 hours at 104° C. in an oven. Weight was recorded from two replicates of 20 kernels.

The results of these studies demonstrate that early stand count was significantly reduced by the early harvest. As shown in Tables 3 and 4, the overall early stand count for black layer harvest was 75%, compared to 60% for the early harvest at the 50% milk line stage. In addition, the early harvest reduced seedling vigor from a value of 4.9 (black layer harvest) to a value of 4.5 (one-half milk line harvest). However, the deleterious effects of early harvest on early stand count were overcome by defoliation at 850 GDD by either manual or chemical defoliation, as shown in Table 4. The dry weight of seed harvested from defoliated plants was only 4% less than the dry weight of seed harvested from non-defoliated plants, indicating that the effect of defoliation on seed size was minimal.

TABLE 3[1]

| Method of Defoliation | Time of Defoliation (GDD) | ESTCNT (%) | SDGVGR | DRYWT (gm) |
|---|---|---|---|---|
| Control | — | 75 | 4.9 | 5.4 |
| Hand | 750 | 73 | 4.9 | 4.4 |
|  | 850 | 78 | 5.1 | 4.9 |
| Paraquat | 750 | 71 | 4.6 | 4.7 |
|  | 850 | 78 | 5.0 | 5.0 |
| Roundup ® | 750 | 74 | 4.8 | 4.8 |
|  | 850 | 77 | 5.1 | 5.2 |

[1]Defoliation time was measured from the pollination date (full silk). Early stand count (ESTCNT), seedling vigor (SDGVGR) and seed dry weight (DRYWT) were determined as described in the text.

TABLE 4[1]

ANALYSIS OF SEED HARVESTED AT THE 50% MILK LINE STAGE

| Method of Defoliation | Time of Defoliation (GDD) | ESTCNT (%) | SDGVGR | DRYWT (gm) |
|---|---|---|---|---|
| Control | — | 60 | 4.5 | 5.1 |
| Hand | 750 | 71 | 4.6 | 4.4 |
|  | 850 | 71 | 4.8 | 4.9 |
| Paraquat | 750 | 63 | 4.5 | 4.6 |
|  | 850 | 67 | 4.6 | 4.9 |
| Roundup ® | 750 | 68 | 4.6 | 4.7 |
|  | 850 | 67 | 4.8 | 4.9 |

[1]Defoliation time was measured from the pollination date (full silk). Early stand count (ESTCNT), seedling vigor (SDGVGR) and seed dry weight (DRYWT) were determined as described in the text.

These results indicate that pre-harvest defoliation of maize at 850 GDD either by hand or with herbicide treatment significantly improved field emergence of maize harvested prior to the black layer stage, while causing only a minimal decrease in seed size.

EXAMPLE 3

Effect of Defoliation by Ignite® or Diquat at 732 or 755 GDD Upon Seed Vigor

In this study, inbred fields were planted in Johnston, Iowa. The inbred, K76, was planted on May 4, while the inbred, T47, was planted on April 30. Chemical defoliation was performed using either 0.38 lb active ingredient Diquat (Valent U.S.A. Corporation)/acre or 0.42 lb active ingredient Ignite® (Hoechst-Roussel Agri-Vet Company)/acre. Chemicals were applied using a high-boy sprayer with two spray drops in 50-foot long strips, covering two rows per strip. Thirty-five gallons of water were used per acre.

The K76 field was sprayed on September 11 at 732 GDD post-pollination and harvested seven days later at 856 GDD post-pollination. The T47 field was sprayed on September 3 at 755 GDD post-pollination and harvested 13 days later at 992 GDD post-pollination.

In these studies, chemical defoliation had the largest impact on the quality of K76 seed. Ignite® and Diquat improved the Cold Test germination of K76 seed by 21% and 19%, respectively. Cold Test germination values for T47 seed improved 8% by Ignite® treatment and 4% by Diquat treatment. Thus, seed quality was improved by pre-harvest defoliation using either Ignite® or Diquat.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. A method for treating a stand of maize plants, comprising the steps of (A) reducing functional leaf area in substantially all of said plants, wherein said reducing is effected at between about 600 and about 850 GDDs after pollination of said plants, and then (B) harvesting said stand, such that a seed assemblage is obtained from said stand that is characterized by a level of seed vigor that is enhanced relative to the level of seed vigor in a seed assemblage harvested from a comparison stand of maize plants not subjected to said reducing of functional leaf area.

2. The method of claim 1, wherein the functional leaf area is reduced by mechanical means.

3. The method of claim 1, wherein the functional leaf area is reduced by chemical means.

4. The method of claim 3, wherein said chemical means comprises a herbicidal formulation.

5. The method of claim 4, wherein said herbicidal formulation comprises a herbicide which is selected from the group consisting of Paraquat, Ignite®, Diquat and Roundup®.

6. The method of claim 5, wherein said herbicidal formulation comprises Ignite®.

7. The method of claim 4, wherein said herbicidal formulation further comprises a surfactant.

* * * * *